(12) United States Patent
Futagawa et al.

(10) Patent No.: US 11,402,344 B2
(45) Date of Patent: Aug. 2, 2022

(54) SOIL SENSOR AND SOIL MEASUREMENT METHOD

(71) Applicant: NATIONAL UNIVERSITY CORPORATION SHIZUOKA UNIVERSITY, Shizuoka (JP)

(72) Inventors: Masato Futagawa, Hamamatsu (JP); Shoji Kawahito, Hamamatsu (JP); Keita Yasutomi, Hamamatsu (JP)

(73) Assignee: NATIONAL UNIVERSITY CORPORATION SHIZUOKA UNIVERSITY

( * ) Notice: Subject to any disclaimer, the term of this patent is extended or adjusted under 35 U.S.C. 154(b) by 127 days.

(21) Appl. No.: 16/756,885

(22) PCT Filed: Oct. 17, 2018

(86) PCT No.: PCT/JP2018/038638
§ 371 (c)(1),
(2) Date: Apr. 17, 2020

(87) PCT Pub. No.: WO2019/082763
PCT Pub. Date: May 2, 2019

(65) Prior Publication Data
US 2021/0199609 A1 Jul. 1, 2021

(30) Foreign Application Priority Data
Oct. 23, 2017 (JP) .............................. JP2017-204337

(51) Int. Cl.
*G01N 27/02* (2006.01)
*G01K 7/00* (2006.01)
*G01N 33/24* (2006.01)

(52) U.S. Cl.
CPC ............... *G01N 27/02* (2013.01); *G01K 7/00* (2013.01); *G01N 33/246* (2013.01); *G01N 2033/245* (2013.01)

(58) Field of Classification Search
CPC ................. G01N 27/02; G01N 33/246; G01N 2033/245; G01K 7/00
(Continued)

(56) References Cited

U.S. PATENT DOCUMENTS

| 5,424,649 A | 6/1995 | Gluck et al. .................. 324/667 |
| 2004/0030606 A1* | 2/2004 | Park ..................... A01G 27/003 700/284 |

(Continued)

FOREIGN PATENT DOCUMENTS

| CA | 1110698 | 10/1981 |
| CA | 1121457 | 4/1982 |

(Continued)

OTHER PUBLICATIONS

International Search Report dated Dec. 25, 2018 in corresponding International Application No. PCT/JP2018/038638.
(Continued)

*Primary Examiner* — Giovanni Astacio-Oquendo
(74) *Attorney, Agent, or Firm* — Ostrolenk Faber LLP

(57) ABSTRACT

A soil sensor includes a current supply unit, an electrode disposed in soil, and a processing unit that obtains a water content and a total ion concentration in the soil. The processing unit includes an information conversion unit that converts a first time and a second time until the measured voltage reaches first threshold voltages and second threshold voltages into frequency information using the temporal change of the measured voltage, an impedance calculation unit that obtains the impedance of the soil, a water content calculation unit that obtains the water content using the
(Continued)

impedance, and a total ion concentration calculation unit that obtains the total ion concentration using the impedance.

11 Claims, 10 Drawing Sheets

(58) Field of Classification Search
USPC .......................................... 324/650, 649, 600
See application file for complete search history.

(56) References Cited

U.S. PATENT DOCUMENTS

| | | | | |
|---|---|---|---|---|
| 2004/0036484 | A1* | 2/2004 | Tamai | G01N 27/225 324/663 |
| 2005/0212532 | A1 | 9/2005 | Bernhard | 324/664 |
| 2009/0219037 | A1 | 9/2009 | Campbell | 324/664 |
| 2011/0316564 | A1 | 12/2011 | Park et al. | 324/672 |
| 2012/0136597 | A1 | 5/2012 | Lin | 702/65 |
| 2015/0147119 | A1* | 5/2015 | Christiansen | G01R 31/3278 405/37 |
| 2020/0358114 | A1* | 11/2020 | Park | H01M 8/04179 |
| 2021/0044034 | A1* | 2/2021 | LaBarge | H01R 4/66 |
| 2021/0236346 | A1* | 8/2021 | Sjöholm | A61F 13/42 |

FOREIGN PATENT DOCUMENTS

| | | |
|---|---|---|
| JP | S55-023484 A | 2/1980 |
| JP | H8-501881 | 2/1996 |
| WO | WO 94/029735 A1 | 12/1994 |

OTHER PUBLICATIONS

International Preliminary Report on Patentability (IPRP) dated May 7, 2020 in corresponding International Application No. PCT/JP2018/038638.
Shin Ogasahara et al.: "Fabrication of a Soil Impedance Sensor with a Shielding Electrode to Measure Low-Level Soil Water Content", *Proceedings of the 33$^{rd}$ Symposium on Sensors, Micromachines, and Applied Systems*, Oct. 17, 2016.
Extended European Search Report dated Jun. 16, 2021 in corresponding European Patent Application No. 18871471.1-1020 / 3702768 PCT/JP2018038638.
De Marcellis A. et al., "A CMOS Integrable Oscillator-Based Front End for High-Dynamic-Range Resistive Sensors", IEEE Transactions on Instrumentation and Measurement, IEEE Service Center, Piscataway, NJ, US, vol. 57, No. 8, Aug. 8, 2008, pp. 1596-1604, XP011226958.
Philips Semiconductors, "NE555 and NE556 applications" Retrieved from the Internet: URL:http://wwwsophphx.caltech.edu/Physics 5/Data sheets/555appnote.pdf [retrieved on Jun. 8, 2021], Dec. 1, 1988, XP055811529.

* cited by examiner

Fig.2
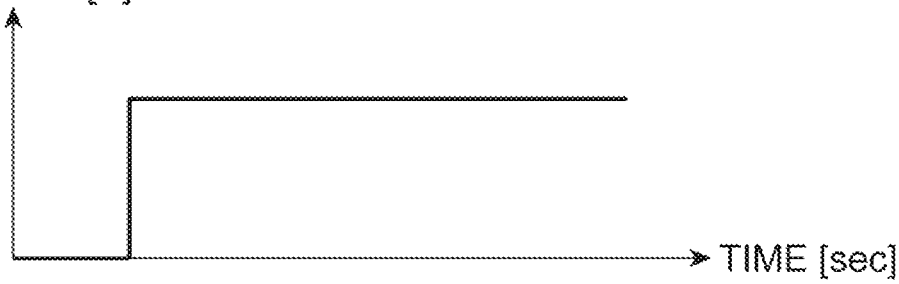
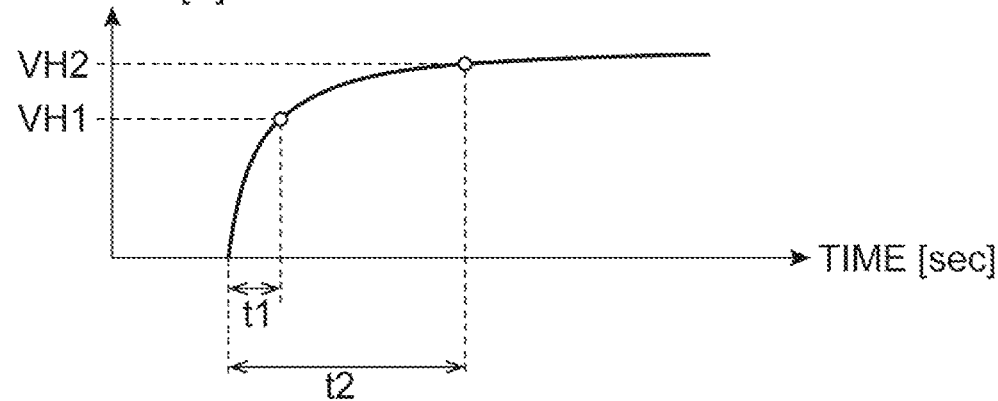

Fig. 8
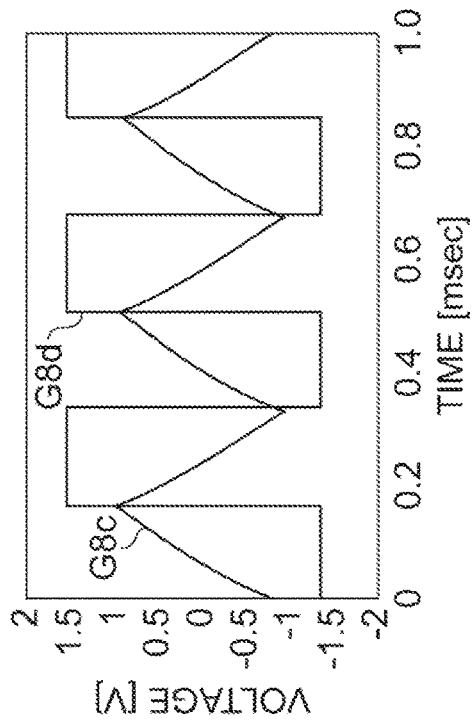
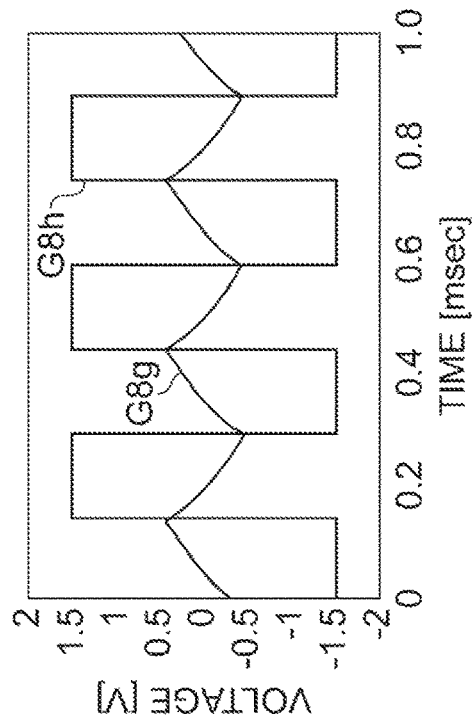
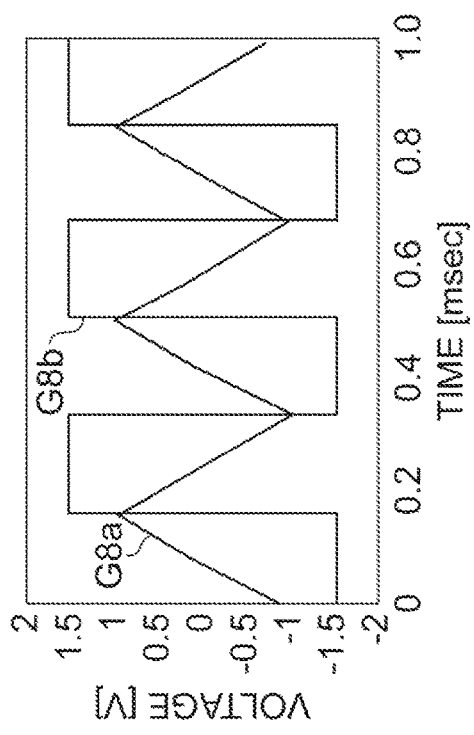
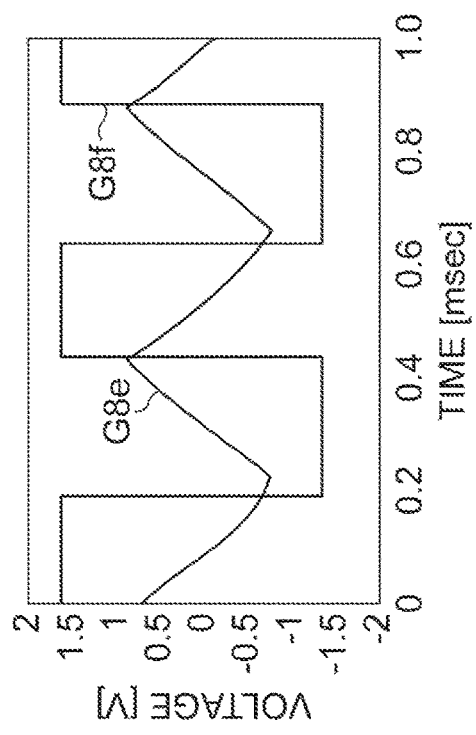

Fig.9
(a)
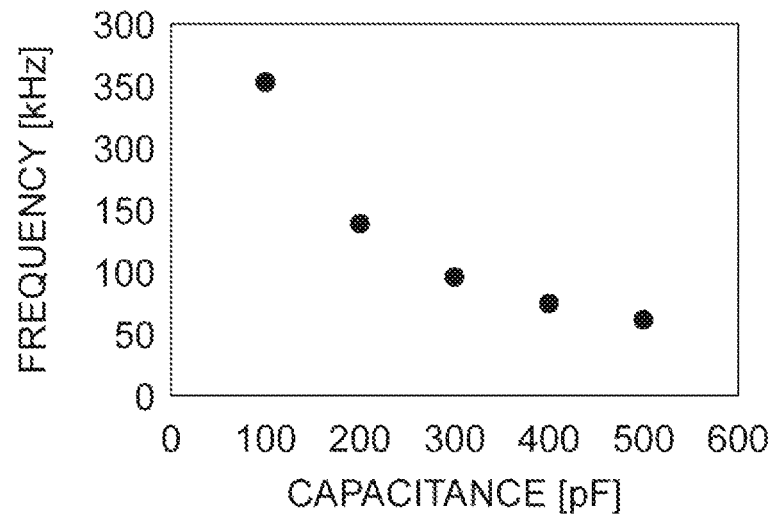
(b)
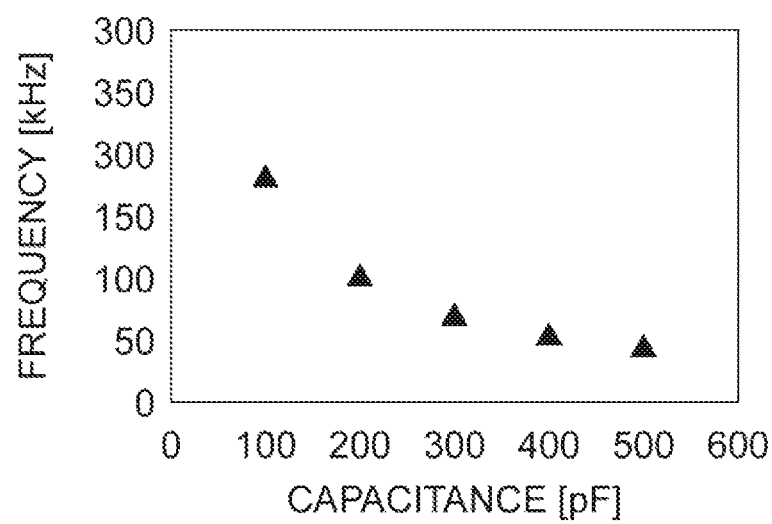

SOIL SENSOR AND SOIL MEASUREMENT METHOD

CROSS-REFERENCE TO RELATED APPLICATIONS

The present application is a 35 U.S.C. §§ 371 national phase conversion of International Application No. PCT/JP2018/038638, filed Oct. 17, 2018, which claims priority to Japanese Patent Application No. 2017-204337, filed Oct. 23, 2017, the contents of both of which are incorporated herein by reference. The PCT International Application was published in the Japanese language.

TECHNICAL FIELD

The present invention relates to a soil sensor and a soil measurement method.

BACKGROUND ART

In recent years, measurement of the water content or ion concentration (nutrient concentration in the agricultural field) in soil has attracted attention in the field of agriculture and disaster prevention. As a method for measuring the water content and ion concentration in soil, a method using electric impedance (for example, see Non Patent Literature 1), a method using the reflection of emitted electromagnetic waves, a method using the propagation speed of temperature, and the like can be mentioned. Among these, a method using electric impedance is mainly used.

CITATION LIST

Non Patent Literature

Non Patent Literature 1: Shin Ogasawara, Masato Futagawa et al., "Development of Shield Electrode Type Soil Impedance Sensor that Enables Measurement of Low-water Soil", Proceedings of the 33rd Symposium on "Sensors, Micromachines, and Applied Systems", Japan, The Institute of Electrical Engineers of Japan, Oct. 17, 2016.

SUMMARY OF INVENTION

Technical Problem

When measuring the water content of soil, the condition of the soil can change from a very dry state to a state in which the soil contains a large amount of water. Therefore, the measurement apparatus requires a wide measurement range. As a result, in the field, a soil sensor and a soil measurement method having a wide measurable range have been desired.

It is an object of the present invention to obtain a soil sensor and a soil measurement method capable of measuring the characteristic values of soil based on a wide measurable range.

Solution to Problem

A soil sensor according to one aspect of the present invention includes: a current supply unit that outputs a DC current; an electrode unit that is connected to the current supply unit and is disposed in soil as a measurement target to supply the DC current to the measurement target; and a processing unit that is connected to the electrode unit and obtains a water content and a total ion concentration in the measurement target using a temporal change of a measured voltage, which is generated in the electrode unit, while the DC current is being supplied to the measurement target, in which the processing unit includes: an information conversion unit that converts time information from when the current supply unit starts supplying the DC current to when an absolute value of the measured voltage reaches an absolute value of a threshold voltage into frequency information by determining whether or not the absolute value of the measured voltage has reached the absolute value of the threshold voltage using the temporal change of the measured voltage; an impedance calculation unit that obtains an impedance of the measurement target using the frequency information, the threshold voltage, and the DC current; a water content calculation unit that obtains the water content using the impedance; and a total ion concentration calculation unit that obtains the total ion concentration using the impedance.

The soil can be modeled as an electric circuit including a resistance component and a capacitance component. In addition, the water content and the total ion concentration in the soil can be obtained based on the resistance component and the capacitance component. The resistance component and the capacitance component can be obtained based on the temporal change of the measured voltage generated in the electrode unit. That is, by using the time until the measured voltage reaches the threshold voltage in the temporal change of the measured voltage, it is possible to calculate the resistance component and the capacitance component that define the temporal change. Then, in order to cause the temporal change of the measured voltage, the soil sensor supplies a DC current from the current supply unit to the electrode unit. The DC current is supplied to the soil as a measurement target through the electrode unit. In the electrode unit, a temporal change of a voltage corresponding to the magnitude of the resistance component and the capacitance component in the soil occurs. As described above, the soil sensor supplies a DC current to the measurement target when calculating the resistance component and the capacitance component. As a result, even when the range of change of the resistance component and the capacitance component is large, it is possible to obtain a good temporal change of a voltage by adjusting the magnitude of the DC current. Therefore, the soil sensor can measure the characteristic values of the soil based on the wide measurable range.

In one aspect, the information conversion unit may output a pulse signal indicating that the absolute value of the measured voltage has reached the absolute value of the threshold voltage, and the current supply unit may switch a direction of the DC current according to the pulse signal. According to this configuration, information based on time regarding the temporal change of the voltage is appropriately converted into information based on the frequency. Since the information based on time is converted into the information based on the frequency, it is possible to increase the resistance to noise.

In one aspect, the DC current may include a first DC current having a positive current value and a second DC current having a negative current value, and the current supply unit may include: a first constant current source that outputs the first DC current; a second constant current source that outputs the second DC current; and a switch that selectively connects one of the first constant current source and the second constant current source to the electrode unit according to the pulse signal. According to this configuration, it is possible to supply a pulsed current that changes periodically to the measurement target. The pulsed current has no limitation in a high frequency range such as a sine wave. As a result, a current having a high frequency can be supplied to the measurement target. Therefore, since it is possible to reduce the influence of an additional capacitance component that may exist before and after the measurement target, it is possible to obtain a better voltage change.

In one aspect, the information conversion unit may include: a first comparator that is connected to the electrode unit and compares the threshold voltage that is positive with the measured voltage; and a second comparator that is connected to the electrode unit and compares the threshold voltage that is negative with the measured voltage. According to this configuration, the information based on time can be converted into the information based on the frequency with a simple configuration.

In one aspect, the information conversion unit may include a logic circuit unit connected to the first comparator and the second comparator. According to this configuration, the information based on time can be converted into the information based on the frequency with a simpler configuration.

In one aspect, the logic circuit unit may include a flip-flop circuit. According to this configuration, the information based on time can be converted into the information based on the frequency with a simpler configuration.

In one aspect, the information conversion unit may include a buffer provided between an output of the first comparator and the impedance calculation unit. According to this configuration, it is possible to reduce the influence of noise on the information transmitted from the information conversion unit to the impedance calculation unit.

In one aspect, the processing unit may further include an amplifier that is disposed between the electrode unit and the first comparator to amplify the measured voltage. According to this configuration, it is possible to eliminate a reading error of the threshold voltage of the comparator when the measured voltage is small.

A soil measurement method according to another aspect of the present invention includes: a step of arranging an electrode unit, which is connected to a current supply unit that outputs a DC current, in soil as a measurement target and then supplying the DC current to the measurement target through the electrode unit; and a step of obtaining a water content and a total ion concentration in the measurement target using a temporal change of a measured voltage, which is generated in the electrode unit, while the DC current is being supplied to the measurement target, in which the step of obtaining the water content and the total ion concentration includes: a step of converting time information from when the current supply unit starts supplying the DC current to when an absolute value of the measured voltage reaches an absolute value of a threshold voltage into frequency information by determining whether or not the absolute value of the measured voltage has reached the absolute value of the threshold voltage using the temporal change of the measured voltage; a step of obtaining an impedance of the measurement target using the frequency information, the threshold voltage, and the DC current; a step of obtaining the water content using the impedance; and a step of obtaining the total ion concentration using the impedance.

Also in this method, when calculating the resistance component and the capacitance component, a DC current is supplied to the measurement target. As a result, even when the range of change of the resistance component and the capacitance component is large, it is possible to obtain a good temporal change of a voltage by adjusting the magnitude of the DC current. Therefore, the soil measurement method can measure the characteristic values of the soil based on the wide measurable range.

In one aspect, the soil sensor may further include a temperature measurement unit that is disposed in the measurement target and that outputs a voltage corresponding to a temperature of the measurement target and supplies the voltage to the processing unit. The processing unit may include: a temperature information conversion unit that receives the voltage supplied from the temperature measurement unit and converts the received voltage into temperature frequency information; and a temperature calculation unit that calculates a temperature of the measurement target using the temperature frequency information output from the temperature information conversion unit.

In one aspect, the temperature measurement unit of the soil sensor may include a diode, and the current supply unit may supply a current to the diode.

A soil sensor according to still another aspect of the present invention includes: a first sensor unit that is disposed in soil as a measurement target and outputs a first measured voltage corresponding to a water content and a total ion concentration in the soil; a second sensor unit that is disposed in soil as the measurement target and outputs a second measured voltage corresponding to a temperature of the soil; an information conversion unit that is selectively connected to the first sensor unit and the second sensor unit and that converts the first measured voltage into first frequency information and converts the second measured voltage into second frequency information; and a measurement value calculation unit that is connected to the information conversion unit and that obtains the water content and the total ion concentration using the first frequency information and obtains the temperature using the second frequency information.

Advantageous Effects of Invention

According to the present invention, a soil sensor and a soil measurement method capable of measuring the characteristic values of soil based on the wide measurement range are provided.

BRIEF DESCRIPTION OF DRAWINGS

FIG. 2(a) is a diagram illustrating an example of a DC current supplied from a current supply unit and FIG. 2(b) is a diagram illustrating an example of a measured voltage generated at an electrode.

FIG. 8(a) is a graph showing a result of Experimental Example 1, FIG. 8(b) is a graph showing a result of Experimental Example 2, FIG. 8(c) is a graph showing a result of Experimental Example 3, and FIG. 8(d) is a graph showing a result of Experimental Example 4.

FIG. 9(a) is a graph showing a result of Experimental Example 5 and FIG. 9(b) is a graph showing a result of Experimental Example 6.

DESCRIPTION OF EMBODIMENTS

Figure 1:
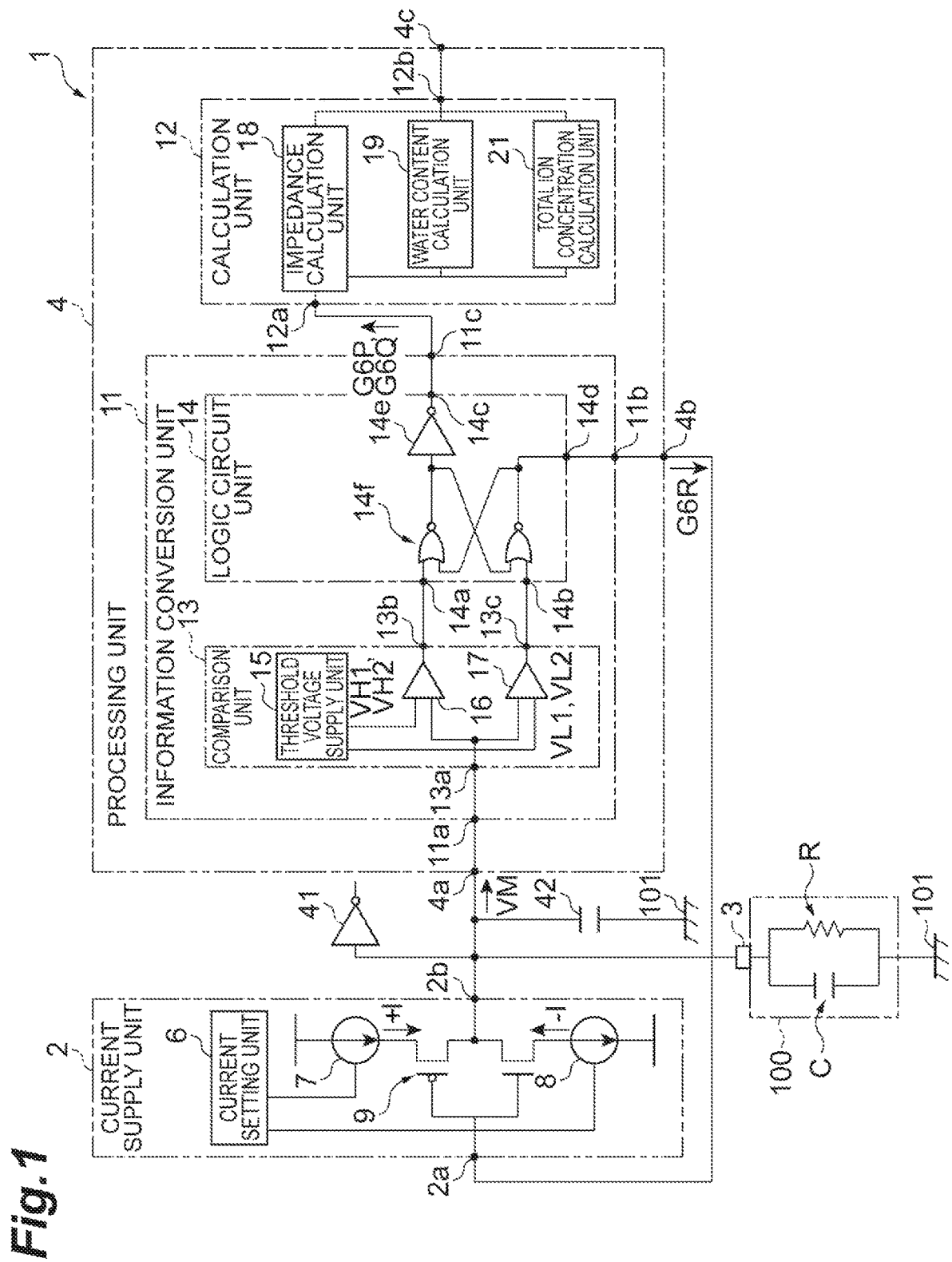
FIG. 1 is a diagram illustrating a configuration of a soil sensor.

Hereinafter, embodiments for carrying out the present invention will be described in detail with reference to the accompanying diagrams. In the description of the diagrams, the same elements are denoted by the same reference numerals, and the repeated description thereof will be omitted.

<Soil Sensor>

As illustrated in FIG. 1, a soil sensor 1 acquires the impedance of soil 100 as a measurement target. The soil 100 includes an electrostatic capacitance (hereinafter, referred to as a "capacitance component C") and an electric resistance (hereinafter, referred to as a "resistance component R") that form the impedance. The soil 100 can be modeled as an electric circuit in which the capacitance component C and the resistance component R are connected in parallel with each other. For example, the size of the capacitance component C of the soil 100 is 10 pF or more and 500 pF or less. In addition, the magnitude of the resistance component R of the soil 100 is 100Ω or more and 1 MΩ or less. Therefore, the soil sensor 1 measures the capacitance component C and the resistance component R in such a wide range. The capacitance component C and the resistance component R are relevant to a water content W and a total ion concentration N of the soil 100. Therefore, the soil sensor 1 can acquire the water content W and the total ion concentration N by acquiring the capacitance component C and the resistance component R. The water content W refers to the ratio of the volume of water in the soil per unit volume. The total ion concentration N refers to the sum of various ions contained in water. For example, the sum of main ions, such as nitrogen ion, phosphate ion, and potassium ion, as the total ion concentration is used in the agricultural field.

The soil sensor 1 includes a current supply unit 2, an electrode 3 (electrode unit), and a processing unit 4. The current supply unit 2 supplies a DC current to the electrode 3. The electrode 3 is inserted into the soil 100. The electrode 3 supplies a DC current (see FIG. 2(a)) to the soil 100. As a result, charges are supplied to the capacitance component C. Therefore, a measured voltage VM received by the electrode 3 increases with time. Then, the measured voltage VM converges to a predetermined value (see FIG. 2(b)). The temporal change of the measured voltage VM is determined by the capacitance component C and the resistance component R. Therefore, the processing unit 4 acquires the capacitance component C and the resistance component R by using the temporal change of the measured voltage VM. In addition, the processing unit 4 acquires the water content W and the total ion concentration N using the capacitance component C and the resistance component R.

In short, the soil sensor 1 has an electrode that detects a voltage generated as a result of applying a constant current to liquid, for example, water or a substance containing the liquid (for example, soil containing water). Then, the soil sensor 1 detects the temporal change of the voltage.

The current supply unit 2 supplies a positive DC current (first DC current) or a negative DC current (second DC current) to the electrode 3. The current supply unit 2 includes an input 2a, an output 2b, a current setting unit 6, a first constant current source 7, a second constant current source 8, and a switch 9.

The output 2b is connected to the electrode 3. The output 2b supplies a DC current to the electrode 3. The input 2a is connected to the processing unit 4. The input 2a receives a control signal from the processing unit 4. The current setting unit 6 controls the first constant current source 7 and the second constant current source 8. As a result, the magnitude of the DC current is determined.

The first constant current source 7 is connected to the switch 9 and the current setting unit 6. The first constant current source 7 generates a positive DC current having a predetermined current value (for example, +1 μA) based on the control signal of the current setting unit 6. The first constant current source 7 supplies the positive DC current to the switch 9.

The second constant current source 8 is connected to the switch 9 and the current setting unit 6. The second constant current source 8 generates a negative DC current (for example, −1 μA) having a predetermined current value based on the control signal of the current setting unit 6. The absolute value of the negative DC current may be the same as the absolute value of the positive DC current in the first constant current source 7. In addition, the absolute value of the negative DC current may be different from the absolute value of the positive DC current in the first constant current source 7. The second constant current source 8 supplies the negative DC current to the switch 9.

The switch 9 is connected to the first constant current source 7, the second constant current source 8, and the output 2b. The switch 9 selectively connects one of the first constant current source 7 and the second constant current source 8 to the output 2b. For example, when the switch 9 connects the first constant current source 7 to the output 2b, the switch 9 does not connect the second constant current source 8 to the output 2b. In this case, the output 2b receives a positive DC current. Conversely, when the switch 9 connects the second constant current source 8 to the output 2b, the switch 9 does not connect the first constant current source 7 to the output 2b. In this case, the output 2b receives a negative DC current. The switch 9 performs switching between a configuration in which the first constant current source 7 is connected to the output 2b and a configuration in which the second constant current source 8 is connected to the output 2b based on a control signal provided from the processing unit 4.

The electrode 3 is disposed so as to be inserted into the soil 100. The electrode 3 supplies a DC current to the soil 100. The electrode 3 is connected to the output 2b of the current supply unit 2 and the processing unit 4.

The processing unit 4 acquires the capacitance component C and the resistance component R by using a temporal change of the measured voltage VM generated at the electrode 3. In addition, the processing unit 4 acquires the water content W and the total ion concentration N. The processing unit 4 includes an input 4a, outputs 4b and 4c, an information conversion unit 11, and a calculation unit 12.

The input 4a is connected to the electrode 3. The input 4a receives a voltage generated at the electrode 3 as the measured voltage VM. The output 4b is connected to the input 2a of the current supply unit 2. The output 4b provides a control signal to the current supply unit 2. The output 4c outputs the capacitance component C, the resistance component R, the water content W, and the total ion concentration N.

The information conversion unit 11 has an input 11a, outputs 11b and 11c, a comparison unit 13, and a logic circuit unit 14. The input 11a is connected to the input 4a of the processing unit 4. The output 11b is connected to the output 4b of the processing unit 4. The output 11c is connected to the calculation unit 12.

The comparison unit 13 compares the measured voltage VM with a threshold value. The comparison unit 13 outputs the result of the comparison as a binary digital value. For example, when the measured voltage VM is smaller than the threshold value, the comparison unit 13 outputs a digital value (0). In addition, when the measured voltage VM is larger than the threshold value, the comparison unit 13 outputs a digital value (1). In addition, when the measured voltage VM is equal to the threshold value, the comparison unit 13 outputs a digital value (1).

The comparison unit 13 includes an input 13a, outputs 13b and 13c, a threshold voltage supply unit 15, a first comparator 16, and a second comparator 17.

The input 13a of the comparison unit 13 is connected to the input 11a of the information conversion unit 11. The input 13a receives the measured voltage VM. The outputs 13b and 13c are connected to the logic circuit unit 14. The output 13b provides a signal received from the first comparator 16 to the logic circuit unit 14. The output 13c provides a signal received from the second comparator 17 to the logic circuit unit 14.

Figure 3:
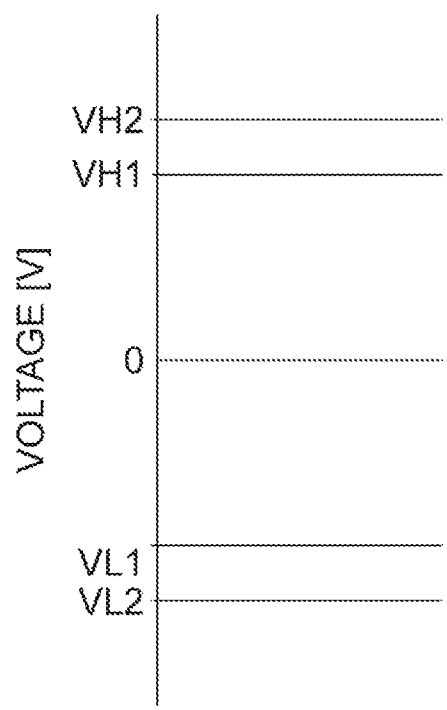
FIG. 3 is a diagram illustrating a relationship between a first threshold voltage and a second threshold voltage.

The threshold voltage supply unit 15 is connected to the first comparator 16 and the second comparator 17. The threshold voltage supply unit 15 supplies a threshold voltage, which is a threshold value, to the first comparator 16 and the second comparator 17. The threshold value includes first threshold voltages VH1 and VL1 and second threshold voltages VH2 and VL2 (see FIG. 3). The first threshold voltage VH1 and the second threshold voltage VH2 are positive voltages. The second threshold voltage VH2 is higher than the first threshold voltage VH1. The first threshold voltage VL1 and the second threshold voltage VL2 are negative voltages. The second threshold voltage VL2 is lower than the first threshold voltage VL1. The absolute value of the first threshold voltage VH1 is equal to the absolute value of the first threshold voltage VL1. The absolute value of the second threshold voltage VH2 is equal to the absolute value of the second threshold voltage VL2. In addition, the absolute values may be different.

The threshold voltage supply unit 15 supplies one of the first threshold voltage VH1 or the second threshold voltage VH2 to the first comparator 16. The threshold voltage supply unit 15 supplies one of the first threshold voltage VL1 and the second threshold voltage VL2 to the second comparator 17. Specifically, when the threshold voltage supply unit 15 supplies the first threshold voltage VH1 to the first comparator 16, the threshold voltage supply unit 15 supplies the first threshold voltage VL1 to the second comparator 17. In addition, when the threshold voltage supply unit 15 supplies the second threshold voltage VH2 to the first comparator 16, the threshold voltage supply unit 15 supplies the second threshold voltage VL2 to the second comparator 17.

The first comparator 16 is connected to the input 13a, the output 13b, and the threshold voltage supply unit 15. When the first threshold voltage VH1 is supplied, the first comparator 16 compares the measured voltage VM with the first threshold voltage VH1. When the second threshold voltage VH2 is supplied, the first comparator 16 compares the measured voltage VM with the second threshold voltage VH2. The first comparator 16 operates as follows. In other words, the first comparator 16 generates a positive maximum voltage (1) when the absolute value of the measured voltage VM is larger than the absolute value of the first threshold voltage VH1 or the second threshold voltage VH2. Then, the first comparator 16 provides a result (0 or 1) of the comparison to the output 13b.

In the case of measured voltage VM<first threshold voltage VH1, negative maximum voltage (0).
In the case of measured voltage VM<second threshold voltage VH2, negative maximum voltage (0).
In the case of measured voltage VM>first threshold voltage VH1, positive maximum voltage (1).
In the case of measured voltage VM>second threshold voltage VH2, positive maximum voltage (1).

The second comparator 17 is connected to the input 13a, the output 13c, and the threshold voltage supply unit 15. When the first threshold voltage VL1 is supplied, the second comparator 17 compares the measured voltage VM with the first threshold voltage VL1. When the second threshold voltage VL2 is supplied, the second comparator 17 compares the measured voltage VM with the second threshold voltage VL2. The second comparator 17 operates as follows. In other words, the second comparator 17 generates a positive maximum voltage (1) when the absolute value of the measured voltage VM is larger than the absolute value of the first threshold voltage VL1 or the second threshold voltage VL2. Then, the second comparator 17 provides a result (0 or 1) of the comparison to the output 13c.

In the case of measured voltage VM>first threshold voltage VL1, negative maximum voltage (0).
In the case of measured voltage VM>second threshold voltage VL2, negative maximum voltage (0).
In the case of measured voltage VM<first threshold voltage VL1, positive maximum voltage (1).
In the case of measured voltage VM<second threshold voltage VL2, positive maximum voltage (1).

The logic circuit unit 14 receives the result of the comparison unit 13 and outputs a pulse signal (see FIG. 6(b)). The logic circuit unit 14 includes a so-called SR flip-flop circuit 14f. That is, the processing unit 4 generates a square wave frequency corresponding to the measured voltage value. The logic circuit unit 14 has inputs 14a and 14b and outputs 14c and 14d. The input 14a is connected to the output 13b of the comparison unit 13. The input 14a is connected to the output 13c of the comparison unit 13. The output 14c is connected to the calculation unit 12. The output 14c provides a pulse signal to the calculation unit 12. A buffer 14e is connected before the output 14c. The buffer 14e inverts an output value. The output 14d is connected to the output 11b.

The logic circuit unit 14 operates as follows.
In the case of input 14a (0) and input 14b (0), output 14c (hold) and output 14d (hold)
In the case of input 14a (0) and input 14b (1), output 14c (1) and output 14d (1)
In the case of input 14a (1) and input 14b (0), output 14c (0) and output 14d (0).

For example, when the measured voltage VM is higher than the set first threshold voltage VH1, the logic circuit unit 14 inverts the values of the outputs 14c and 14d. For example, when the output 14c of the logic circuit unit 14 is (0) and the output 14d is (0), the output 14c is switched from (0) to (1) if the conditions are satisfied. The output 14d is switched from (0) to (1).

The output 14d is connected to the switch 9 of the current supply unit 2 through the output 11d and the output 4b. Therefore, when the value of the output 14d is inverted, the switch 9 is switched. That is, the output of the current supply unit 2 is switched from the positive DC current to the negative DC current. Alternatively, the output of the current supply unit 2 is switched from the negative DC current to the positive DC current.

The calculation unit 12 acquires the capacitance component C, the resistance component R, the water content W, and the total ion concentration N using the pulse signal provided from the logic circuit unit 14. The calculation unit 12 includes an input 12a, an output 12b, an impedance calculation unit 18, a water content calculation unit 19, and a total ion concentration calculation unit 21.

The input 12a is connected to the output 11c of the information conversion unit 11. The input 12a receives an input signal as a pulse signal from the information conversion unit 11. The output 13b is connected to the impedance calculation unit 18, the water content calculation unit 19, and the total ion concentration calculation unit 21. The input 12a outputs various kinds of information.

The impedance calculation unit 18 calculates an impedance using the pulse signal, the first threshold voltages VH1 and VL1, the second threshold voltages VH2 and VL2, and a DC current I. The pulse signal is obtained from the logic circuit unit 14. The first threshold voltages VH1 and VL1 and the second threshold voltages VH2 and VL2 are obtained from the threshold voltage supply unit 15. The DC current I is obtained from the current setting unit 6.

Figure 4:
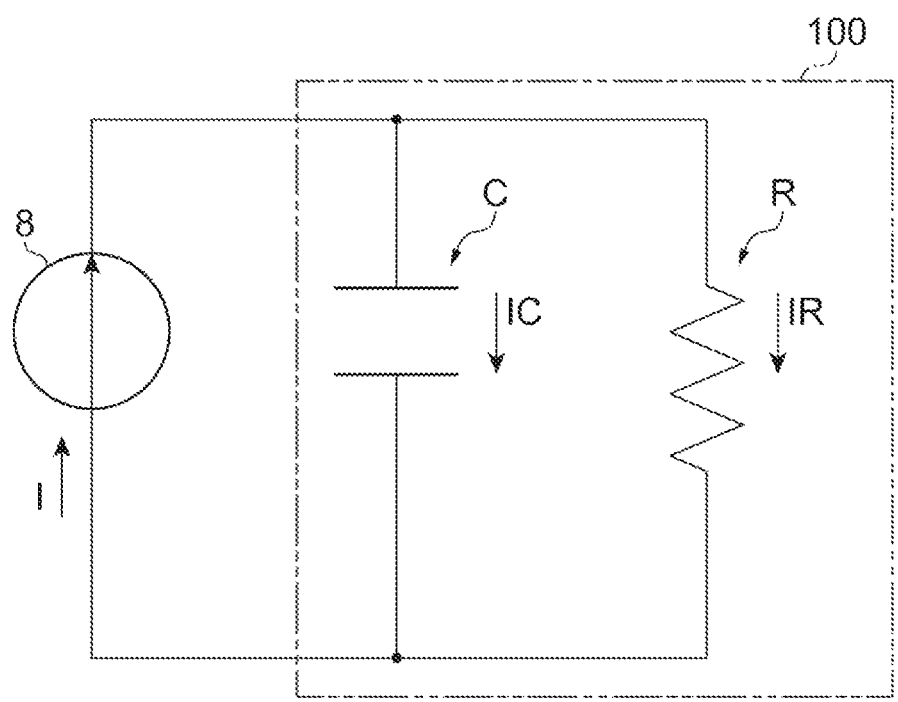
FIG. 4 is a diagram illustrating a circuit model of soil for describing the operation principle of an impedance calculation unit.

The operation of the impedance calculation unit 18 will be described in detail. FIG. 4 illustrates an electric circuit obtained by modeling the second constant current source 8 and the soil 100. In this electric circuit, the current in each element is expressed by the following equations. Equation (1) is a current (IC) in the capacitance component C. Equation (2) is a current (IR) in the resistance component R.

[Equation 1]
$$I_C = C\frac{dV_C}{dt} \quad (1)$$

[Equation 2]
$$I_R = \frac{V_C}{R} \quad (2)$$

The relationship between the DC current I in the second constant current source 8 and the current (IC) and the current (IR) is expressed by the following equation.

[Equation 3]
$$I = I_C + I_R = C\frac{dV_C}{dt} + \frac{V_C}{R} \quad (3)$$

Then, by modifying the above equation, the following equation is obtained.

[Equation 4]
$$I = \frac{CV_C}{t} + \frac{V_C}{R} = \left(\frac{C}{t} + \frac{1}{R}\right)V_C \quad (4)$$

Here, as illustrated in FIG. 2(b), it is assumed that the time until reaching the first threshold voltage VH1 is a first time t1. In addition, it is assumed that the time until reaching the second threshold voltage VH2 is t2. Then, the following equation is obtained.

[Equation 5]
$$\begin{cases} \frac{I}{V_{H1}} = \frac{C}{t_1} + \frac{1}{R} \\ \frac{I}{V_{H2}} = \frac{C}{t_2} + \frac{1}{R} \end{cases} \quad (5)$$

In the above equation, the capacitance component C and the resistance component R are unknown. The first threshold voltage VH1, the second threshold voltage VH2, the first time t1, the second time t2, and the DC current I are known. Therefore, the above equation is treated as simultaneous equations to calculate the capacitance component C and the resistance component R. As a result, the following equations are obtained.

[Equation 6]
$$C = \frac{t_2 t_1 (V_{H1} - V_{H2})}{V_{H2} V_{H1} (t_1 - t_2)} \quad (6)$$

[Equation 7]
$$R = \frac{V_{H1} t_1}{It_1 - CV_{H1}} \quad (7)$$

By substituting the first threshold voltage VH1, the second threshold voltage VH2, the first time t1, the second time t2, and the DC current I into the above Equations (6) and (7), the capacitance component C and the resistance component R are obtained. That is, the impedance calculation unit 18 calculates the capacitance component C and the resistance component R using Equations (6) and (7), the first threshold voltage VH1, the second threshold voltage VH2, the first time t1, the second time t2, and the DC current I.

The water content calculation unit 19 is connected to the impedance calculation unit 18. The water content calculation unit 19 receives the capacitance component C and the resistance component R from the impedance calculation unit 18. The water content calculation unit 19 calculates the water content W using the capacitance component C. The relative permittivity $\varepsilon_S$ in the capacitance component C is determined by the relative permittivity of water, the relative permittivity of air, and the relative permittivity of soil. That is, the relative permittivity $\varepsilon_S$ is an apparent value obtained by combining the relative permittivity of water, the relative permittivity of air, and the relative permittivity of soil. For example, the relative permittivity of water is about 80. The relative permittivity of air is about 1. The relative permittivity of soil is 3 or more and 7 or less. The impedance calculation unit 18 calculates the ratio of each relative permittivity to the relative permittivity $\varepsilon_S$ using this method, and acquires the volume water content of water from the ratio. For example, it can be assumed that the capacitance component C of soil M is almost the capacitance component of water. According to this assumption, the capacitance component C of the soil M can be regarded as a product of the water content W and the relative permittivity $\varepsilon_S$. Therefore, the water content W can be obtained by dividing the capacitance component C of the soil M by the relative permittivity $\varepsilon_S$.

The total ion concentration calculation unit 21 is connected to the impedance calculation unit 18. The total ion concentration calculation unit 21 receives the capacitance component C and the resistance component R from the impedance calculation unit 18. The total ion concentration calculation unit 21 calculates the total ion concentration using the capacitance component C and the resistance component R. The total ion concentration calculation unit 21 calculates the total ion concentration N by dividing the resistance component R by the water content W using the water content W calculated based on the capacitance component C. For example, the resistance component R of the soil M is assumed to be the product of the water content W and the total ion concentration N. The water content W is obtained by the water content calculation unit 19. The resistance component R is obtained by the impedance calculation unit 18. As a result, the total ion concentration N is obtained by dividing the resistance component R by the water content W.

Figure 5:
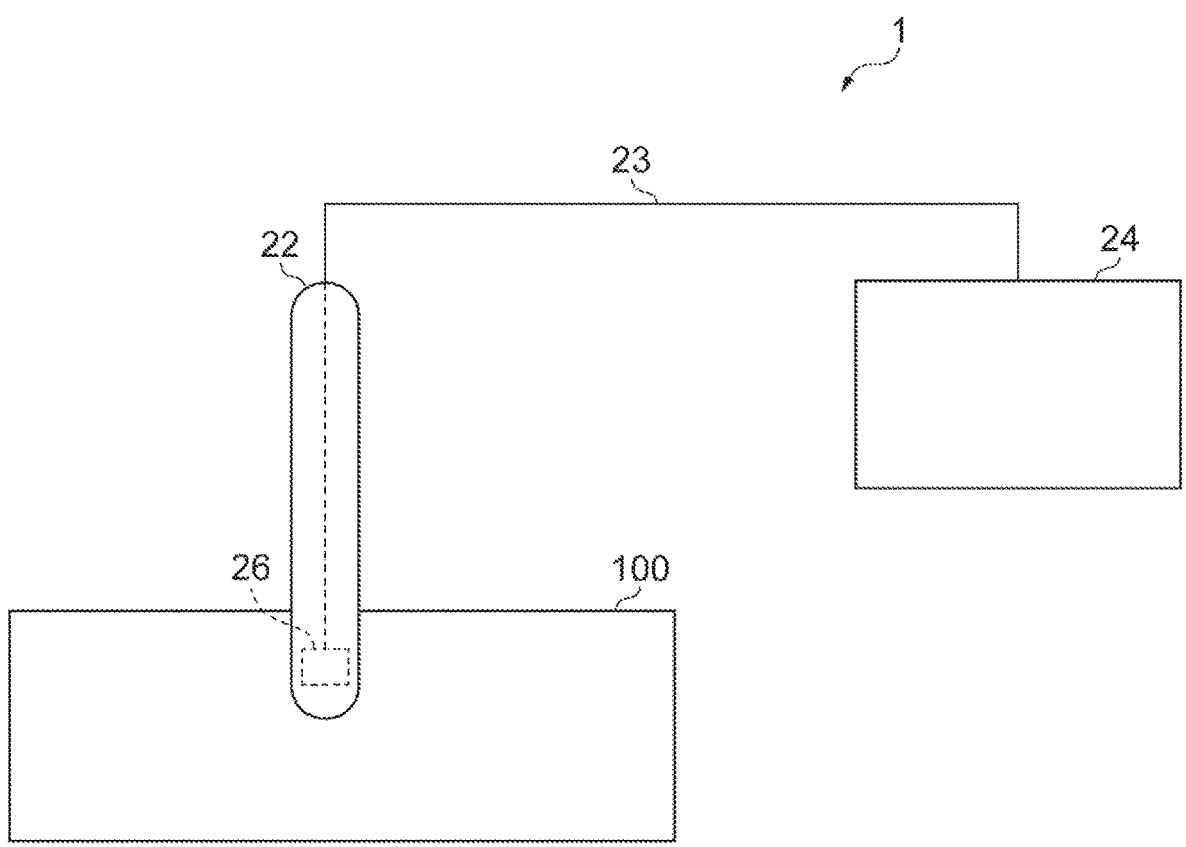
FIG. 5 is a diagram illustrating a specific configuration example of the soil sensor.

FIG. 5 illustrates a specific configuration of the soil sensor 1. As illustrated in FIG. 5, the soil sensor 1 has a probe 22, a cable 23, and a computer 24. The probe 22 is a rod-shaped component inserted into the soil 100. At the distal end of the probe 22, a sensor chip 26 is provided. The sensor chip 26 is embedded in the soil 100. The sensor chip 26 includes the current supply unit 2, the electrode 3, and the information conversion unit 11. For example, the sensor chip 26 may be an IC chip. One end of the cable 23 is connected to the rear end of the probe 22. The other end of the cable 23 is connected to the computer 24 provided at a position away from the probe 22. The signal output from the probe 22 is provided to the computer 24 through the cable 23. The probe 22 and the computer 24 may be connected to each other by wireless communication.

The sensor chip 26 includes the information conversion unit 11. Therefore, the signal output from the sensor chip 26 is a pulse signal. That is, the signal output from the sensor chip 26 is a binary digital signal. Therefore, even when there is a physical distance between the sensor chip 26 and the computer 24, it is possible to improve the resistance to noise regardless of wired or wireless.

The computer 24 includes the impedance calculation unit 18, the water content calculation unit 19, and the total ion concentration calculation unit 21 that have been described. The impedance calculation unit 18, the water content calculation unit 19, and the total ion concentration calculation unit 21 may be functional components realized by executing a program by the computer 24. According to such a configuration, even the complicated and various voltage characteristics can be handled by adjusting the algorithm, so that the resistance component R and the capacitance component C can be easily calculated. The computer 24 is not particularly limited as long as it is possible to execute a program for the impedance calculation unit 18, the water content calculation unit 19, and the total ion concentration calculation unit 21. For example, the computer 24 may be a portable information terminal such as a personal computer, a laptop computer, and a smartphone.

Hereinafter, the operation of the soil sensor 1 will be described.

The switch 9 connects one of the first constant current source 7 and the second constant current source 8 to the electrode 3. As an initial setting, the second constant current source 8 is connected to the electrode 3. In addition, the first constant current source 7 may be connected to the electrode 3 as an initial setting.

The current setting unit 6 sets the magnitude of the current. For example, the first threshold voltage VH1 and the second threshold voltage VH2 are set to easily controllable voltages (for example, 0.5 V). In this state, the frequency signal is observed while gradually increasing the current value. Then, a current value at which a desired frequency signal can be obtained is determined as a set value. In the processing unit 4, the first threshold voltage VH1 is supplied from the threshold voltage supply unit 15 in the comparison unit 13 to the first comparator 16. In addition, the processing unit 4 supplies the first threshold voltage VL1 to the second comparator 17. For example, an inflection point deviating from a linear change is searched for while gradually increasing the first threshold voltages VH1 and VL1. The first threshold voltages VH1 and VL1 may be determined based on the result of the search for the inflection point.

The operations of the first constant current source 7 and the second constant current source 8 are started. The first constant current source 7 outputs a positive DC current. The second constant current source 8 outputs a negative DC current. The second constant current source 8 is connected to the electrode 3. As a result, the electrode 3 receives a negative DC current.

Figure 6:
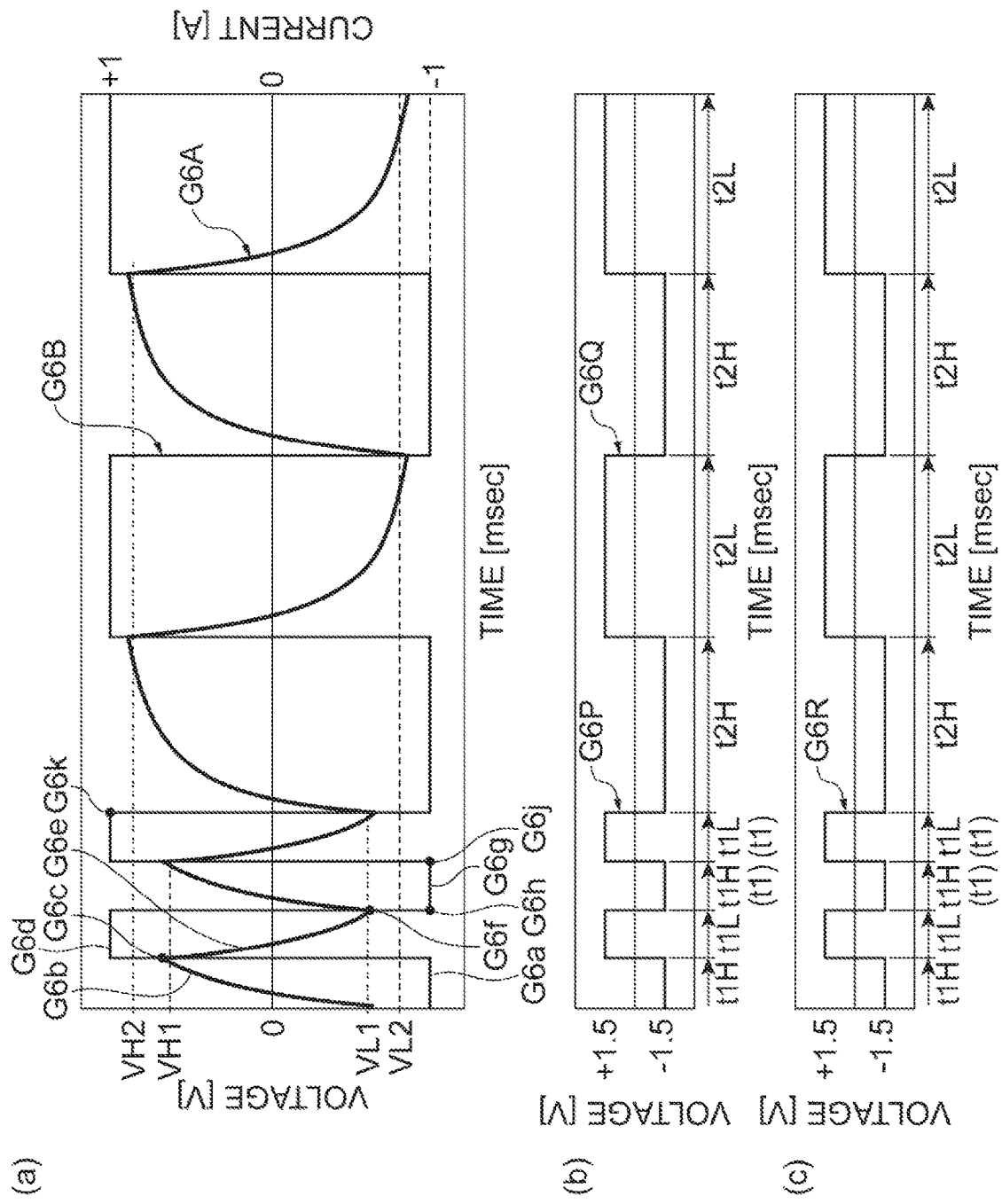
FIG. 6(a) is a graph showing a temporal change of a DC current and a temporal change of a measured voltage.
FIG. 6(b) is a graph showing a pulse signal.
FIG. 6(c) is a graph showing a control signal.

FIG. 6(a) is a graph showing a temporal change of the DC current supplied from the measured voltage VM and a temporal change of the DC current supplied from the current supply unit 2. In FIG. 6(a), a graph G6A shows the measured voltage VM. A graph G6B shows the DC current supplied to the electrode 3. FIG. 6(b) is an example of a pulse signal output from the output 14c of the information conversion unit 11. FIG. 6(c) is an example of a control signal G6R output from the output 14d of the information conversion unit 11. When a negative DC current is supplied to the electrode 3 (see a G6a part in FIG. 6), a voltage (measured voltage VM) between the electrode 3 and a reference potential 101 increases with time (see a G6b part in FIG. 6). The measured voltage VM is supplied to each of the first comparator 16 and the second comparator 17.

The first comparator 16 compares the measured voltage VM with the first threshold voltage VH1. The measured voltage VM is initially smaller than the first threshold voltage VH1 (VM<VH1). Therefore, the first comparator 16 outputs a minimum voltage (for example, −1.5 V) (digital value (0)). In the following description, it is assumed that the digital value (0) is a voltage value of −1.5 V, for example. In addition, it is assumed that the digital value (1) is, for example, a voltage value of +1.5 V.

The second comparator 17 compares the measured voltage VM with the first threshold voltage VL1. The measured voltage VM increases with time. The measured voltage VM is higher than the first threshold voltage VL1 (VM>VL1). Therefore, the second comparator 17 outputs a minimum voltage (digital value (0)).

The input 14a of the logic circuit unit 14 receives a digital value (0). The input 14b of the logic circuit unit 14 receives a digital value (0). Therefore, the logic circuit unit 14 maintains the state at the outputs 14c and 14d. For example, the logic circuit unit 14 maintains digital values (output 14c (0), output 14d (0)) as initial values.

The measured voltage VM increases with time. Then, it is assumed that the measured voltage VM exceeds the first threshold voltage VH1 (see a G6c part in FIG. 6). In the second comparator 17, the magnitude relationship between the measured voltage VM and the first threshold voltage VL1 does not change (VM>VL1). As a result, the second comparator 17 outputs a minimum voltage (digital value (0)).

In the first comparator 16, the magnitude relationship between the measured voltage VM and the first threshold voltage VH1 is reversed (VM>VH1). The first comparator 16 outputs a maximum voltage (for example, +1.5 V) (digital value (1)).

The input 14a of the logic circuit unit 14 receives a digital value (1). The input 14b of the logic circuit unit 14 receives a digital value (0). The digital values generated at the outputs 14c and 14d are reversed. The logic circuit unit 14 generates a digital value (1) at the output 14c. The logic circuit unit 14 generates a digital value (1) at the output 14d.

The polarity of the pulse signal generated at the output 14c is reversed (see FIG. 6(b)). In addition, the polarity of the pulse signal provided from the output 14d to the switch 9 is also reversed (see FIG. 6(c)). Therefore, the switch 9 releases the connection between the second constant current source 8 and the electrode 3. The switch 9 connects the first constant current source 7 to the electrode 3. By this connection switching, the electrode 3 receives a positive DC current (see a G6d part in FIG. 6). In addition, it is assumed that "when the current supply unit starts supplying the DC current" in the present disclosure includes a case where the direction of the DC current supplied to the electrode 3 is reversed.

When a positive DC current is supplied to the electrode 3, the voltage between the electrode 3 and the reference potential 101 decreases with time (see a G6e part in FIG. 6).

The first comparator 16 compares the measured voltage VM with the first threshold voltage VH1. The measured voltage VM is initially smaller than the first threshold voltage VH1 (VM<VH1). Therefore, the first comparator 16 outputs a minimum voltage (digital value (0)).

The second comparator 17 compares the measured voltage VM with the first threshold voltage VL1. The measured voltage VM decreases with time. The measured voltage VM is initially higher than the first threshold voltage VL1 (VM>VL1). The second comparator 17 outputs a minimum voltage (digital value (0)).

The input 14a of the logic circuit unit 14 receives a digital value (0). The input 14b of the logic circuit unit 14 receives a digital value (0). Therefore, the logic circuit unit 14 maintains the states of the outputs 14c and 14d.

The measured voltage VM decreases with time. Then, it is assumed that the measured voltage VM falls below the first threshold voltage VL1 (see a G6f part in FIG. 6). In the first comparator 16, the magnitude relationship between the measured voltage VM and the first threshold voltage VH1 does not change (VM<VH1). As a result, the first comparator 16 outputs a minimum voltage (digital value (0)).

In the second comparator 17, the magnitude relationship between the measured voltage VM and the first threshold voltage VL1 is reversed (VM<VL1). As a result, the second comparator 17 outputs a maximum voltage (digital value (1)).

The input 14a of the logic circuit unit 14 receives a digital value (0). The input 14b of the logic circuit unit 14 receives a digital value (1). The digital values generated at the outputs 14c and 14d are reversed. The logic circuit unit 14 generates a digital value (0) at the output 14c. The logic circuit unit 14 generates a digital value (0) at the output 14d.

Therefore, the polarity of the pulse signal generated at the output 14c is reversed. The polarity of the pulse signal provided from the output 14d to the switch 9 is also reversed. The switch 9 releases the connection between the first constant current source 7 and the electrode 3. The switch 9 connects the second constant current source 8 to the electrode 3. By this connection switching, the electrode 3 receives a positive DC current (see a G6g part in FIG. 6).

The soil sensor 1 repeats the above operation for a predetermined time.

As a result of the repetition, a pulse signal G6P shown in FIG. 6(b) is obtained. According to the pulse signal G6P, the time during which the polarity is maintained (the time until the polarity is inverted) corresponds to the time (first time t1H) required for the measured voltage VM to reach the first threshold voltage VL1. Similarly, the time during which the polarity is maintained (the time until the polarity is inverted) corresponds to the time (first time t1L) required for the measured voltage VM to reach the first threshold voltage VL1. The period of the pulse signal G6P corresponds to the first time t1.

The processing unit 4 controls the threshold voltage supply unit 15 to change the first threshold voltages VH1 and VL1 to the second threshold voltages VH2 and VL2. For example, the second threshold voltages VH2 and VL2 may be points where both the resistance component R and the capacitance component C appear. In the case of only the capacitance component C, (second threshold voltage÷ first threshold voltage)=(first frequency÷ second frequency). On the other hand, for a voltage including the resistance component R, (second threshold voltage÷ first threshold voltage) <(first frequency÷ second frequency). As a result, the second threshold voltages VH2 and VL2 may be set such that first frequency÷ second frequency becomes a sufficiently large value. The current setting unit 6 maintains the initial setting. The comparison unit 13 and the logic circuit unit 14 perform the same operation as when the first threshold voltages VH1 and VL1 are used. As a result, a pulse signal G6Q as shown in FIG. 6 is obtained.

The second threshold voltage VH2 is higher than the first threshold voltage VH1. Therefore, the second time t2H required for the measured voltage VM to reach the second threshold voltage VH2 is longer than the first time t1H required for the measured voltage VM to reach the first threshold voltage VH1. Similarly, the second time t2L required for the measured voltage VM to reach the second threshold voltage VL2 is longer than the first time t1L required for the measured voltage VM to reach the first threshold voltage VL1.

As described above, the impedance calculation unit 18 obtains the capacitance component C and the resistance component R by the following equations.

[Equation 8]
$$C = \frac{t_2 t_1 (V_{H1} - V_{H2})}{V_{H2} V_{H1} (t_1 - t_2)} \quad (6)$$

[Equation 9]
$$R = \frac{V_{H1} t_1}{I t_1 - C V_{H1}} \quad (7)$$

The water content calculation unit 19 obtains the water content W by dividing the capacitance component C of the soil M by the relative permittivity $\varepsilon_S$ as described above.

The total ion concentration calculation unit 21 obtains the total ion concentration N by dividing the resistance component R by the water content W as described above.

Through the above operation, the soil sensor 1 obtains the water content W and the total ion concentration N.

<Soil Measurement Method>

Figure 7:
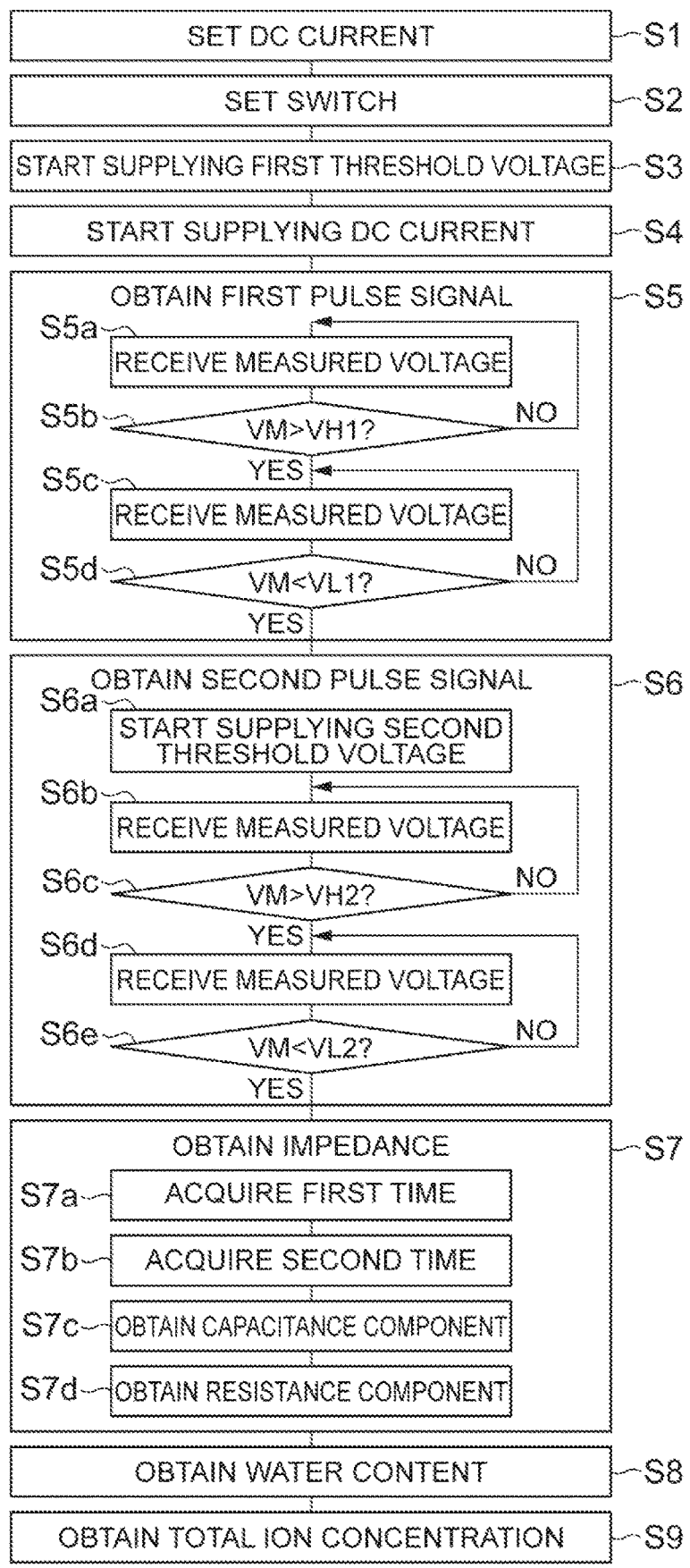
FIG. 7 is a flowchart illustrating main steps of a soil measurement method.

A soil measurement method will be described with reference to the flowchart illustrated in FIG. 7. The soil measurement method is executed by operating the soil sensor 1 described above. For example, the processing unit 4 in the soil sensor 1 is realized by executing an algorithm. This algorithm calculates the resistance component R and the capacitance component C from the measured frequency and the set current and voltage.

A step of setting a DC current (S1) is performed. The step S1 is performed by the current setting unit 6. For example, the current setting unit 6 sets a DC current output from the first constant current source 7 to +1 µA. In addition, the current setting unit 6 sets a DC current output from the second constant current source 8 to −1 µA.

A step of setting a switch (S2) is performed. The step S2 is performed by the current supply unit 2. For example, the current supply unit 2 controls the switch 9 so that the second constant current source 8 is connected to the electrode 3.

A step of starting to supply a first threshold voltage (S3) is performed. The step S3 is performed by the threshold voltage supply unit 15. For example, the threshold voltage supply unit 15 supplies +0.5 V to the first comparator 16 as the first threshold voltage VH1. In addition, the threshold voltage supply unit 15 supplies −0.5 V to the second comparator 17 as the first threshold voltage VL1.

The steps S1, S2, and S3 described above are preparatory steps before starting the measurement.

A step of starting to supply a DC current (S4) is performed. The step S4 is performed by the current supply unit 2. By the step S4, the supply of a DC current to the electrode 3 is started. By the step S4, the measurement is started.

A step of obtaining a first pulse signal (S5) is performed. The step S5 includes a step of receiving the measured voltage VM (S5a), a step of comparing the measured voltage VM with the first threshold voltage VH1 (S5b), a step of receiving the measured voltage VM (S5c), and a step of comparing the measured voltage VM with the first threshold voltage VL1 (S5d).

The step S5a is performed. When the supply of the negative DC current to the electrode 3 is started, the processing unit 4 receives the measured voltage VM from the input 4a (S5a).

The step S5b is performed. The step S5b is performed by the comparison unit 13 and the logic circuit unit 14. The measured voltage VM is supplied to the first comparator 16. The first comparator 16 compares the measured voltage VM with the first threshold voltage VH1 (S5b). Specifically, it is determined whether or not the absolute value of the measured voltage VM is larger than the absolute value of the first threshold voltage VH1.

As a result of the determination, when the measured voltage VM is not higher than the positive first threshold voltage VH1 (S5b: NO, VM<VH1), the logic circuit unit 14 maintains the output state. Then, after a predetermined time has passed, the steps S5a and S5b are performed again.

When the measured voltage VM is higher than the positive first threshold voltage VH1 (S5b: YES, VM>VH1), the logic circuit unit 14 inverts the values of the outputs 14c and 14d. The switch 9 operates according to the result of the inversion of the value of the output 14d. As a result, the electrode 3 starts receiving a positive DC current.

The step S5c is performed. When the electrode 3 starts receiving the DC current, the processing unit 4 receives the measured voltage VM from the input 4a (S5c).

The step S5d is performed. The step S5d is performed by the comparison unit 13 and the logic circuit unit 14. The measured voltage VM is supplied to the second comparator 17. The second comparator 17 compares the measured voltage VM with the first threshold voltage VL1 (S5d). Specifically, it is determined whether or not the absolute value of the measured voltage VM is greater than the absolute value of the first threshold voltage VL1.

As a result of the determination, when the measured voltage VM is higher than the negative first threshold voltage VH1 (S5d: NO, VM>VL1), the logic circuit unit 14 maintains the output state. Then, after a predetermined time has passed, the steps S5c and S5d are performed again.

When the measured voltage VM is lower than the negative first threshold voltage VL1 (S5d: YES, VM<VL1), the logic circuit unit 14 inverts the values of the outputs 14c and 14d. The switch 9 operates according to the result of the inversion of the value of the output 14d. As a result, the electrode 3 starts receiving a negative DC current.

A step of obtaining a second pulse signal (S6) is performed. The step S6 includes a step of starting to supply the second threshold voltage VH2 (S6a), a step of receiving the measured voltage VM (S6b), a step of comparing the measured voltage VM with the second threshold voltage VH2 (S6c), a step of receiving the measured voltage VM (S6d), and a step of comparing the measured voltage VM with the second threshold voltage VL2 (S6e).

The step of starting to supply the second threshold voltage (S6a) is performed. The step S6a is performed by the threshold voltage supply unit 15. For example, the threshold voltage supply unit 15 supplies +1 V to the first comparator 16 as the second threshold voltage VH2. In addition, the threshold voltage supply unit 15 supplies −1 V to the second comparator 17 as the second threshold voltage VL2.

The step S6b is performed. When the electrode 3 starts receiving the DC current, the processing unit 4 receives the measured voltage VM from the input 4a (S6b).

The step S6c is performed. The step S6c is performed by the comparison unit 13 and the logic circuit unit 14. The first comparator 16 receives the measured voltage VM. That is, the first comparator 16 compares the measured voltage VM with the second threshold voltage VH2 (S6c). Specifically, the first comparator 16 determines whether or not the absolute value of the measured voltage VM is larger than the absolute value of the second threshold voltage VH2.

When the measured voltage VM is not higher than the positive second threshold voltage VH2 (S6c: NO, VM<VH2), the logic circuit unit 14 maintains the state of the outputs 14c and 14d. Then, after a predetermined time has passed, the steps S6b and S6c are performed again.

When the measured voltage VM is higher than the positive second threshold voltage VH2 (S6c: YES, VM>VH1), the logic circuit unit 14 inverts the values of the outputs 14c and 14d. The switch 9 operates according to the result of the inversion of the value of the output 14d. As a result, the electrode 3 starts receiving a reverse DC current.

The step S6d is performed. When the supply of the DC current to the electrode 3 is started, the processing unit 4 receives the measured voltage VM from the input 4a (S6d).

The step S6f is performed. The step S6f is performed by the comparison unit 13 and the logic circuit unit 14. The second comparator 17 receives the measured voltage VM. The second comparator 17 compares the measured voltage VM with the second threshold voltage VL2 (S6f). Specifically, the second comparator 17 determines whether or not the absolute value of the measured voltage VM is larger than the absolute value of the second threshold voltage VL2.

When the measured voltage VM is higher than the second threshold voltage VH2 (S6f: NO, VM>VL1), the logic circuit unit 14 maintains the state of the outputs 14c and 14d.

Then, after a predetermined time has passed, the steps S6*d* and S6*e* are performed again.

When the measured voltage VM is lower than the second threshold voltage VL2 (S6*f*: YES, VM<VL1), the logic circuit unit 14 inverts the values of the outputs 14*c* and 14*d*. The switch 9 operates according to the result of the inversion of the value of the output 14*d*. As a result, the electrode 3 starts receiving a reverse DC current.

A step of obtaining impedance (S7) is performed. The step S7 is performed by the impedance calculation unit 18. The step S7 includes a step of acquiring the first time t1 (S7*a*), a step of acquiring the second time t2 (S7*b*), a step of obtaining the capacitance component C (S7*c*), and a step of obtaining the resistance component R (S7*d*).

The step S7*a* is performed. In step S7*a*, the first time t1 is obtained. The first time t1 is an elapsed time from a timing at which the supply of a negative DC current is started (see a G6*h* part in FIG. 6(*a*)) to a timing at which switching to a positive DC current occurs (see a G6*j* part in FIG. 6(*a*)). In addition, the first time t1 may be an elapsed time from a timing at which the supply of a positive DC current is started (G6*j* part) to a timing at which switching to a negative DC current occurs (G6*k* part).

The step S7*b* is performed. Similarly to the step S7*a*, the second time t2 is obtained based on the timing at which the polarity of the current is switched.

The step S7*c* is performed. The step S7*c* is performed by the impedance calculation unit 18.

The step S7*d* is performed. The step S7*d* is also performed by the impedance calculation unit 18.

A step of obtaining the water content W (S8) is performed. The step S8 is performed by the water content calculation unit 19.

The step of obtaining the total ion concentration N (S9) is performed. The step S9 is performed by the total ion concentration calculation unit 21.

Through the above steps S1 to S9, the capacitance component C, the resistance component R, the water content W, and the total ion concentration N that indicate the characteristics of the soil 100 are obtained.

Hereinafter, the operational effects of the soil sensor 1 will be described.

In the field of agriculture and disaster prevention, it is very important to measure the water content and ion concentration (nutrient concentration in the agricultural field) in soil. As a method for measuring the water content and ion concentration in soil, a method using electric impedance, a method using the reflection of emitted electromagnetic waves, a method using the propagation speed of temperature, and the like can be mentioned. The method using impedance has higher measurement accuracy than the method using the temperature. In addition, the method using impedance consumes less power than the method using the reflection of electromagnetic waves.

In general, when measuring impedance, a sine wave (single frequency) of voltage or current is applied to a measurement target. The impedance can be obtained using a current or a voltage obtained as a result of applying a voltage or a current. The impedance (Z) of soil and water is shown as $Z=1/(1/R+j\omega C)$. The resistance component R and the capacitance component C can be calculated using the measurement result of the sine wave (absolute value |Z| of the impedance, phase $\Theta$, and frequency f).

According to this method, the impedance (Z) can be accurately calculated. However, the range in which the water content and the total ion concentration in soil change is large. Therefore, there is a possibility that the resistance component R and the capacitance component C will also change significantly depending on the water content and the total ion concentration. When the resistance component R and the capacitance component C also change significantly, it is difficult to perform measurement in the entire change range by measurement using a single frequency. Soil having a low water content has high impedance. As a result, a signal to be measured becomes weak. Therefore, a true signal component may be hidden by a noise component in the soil having a low water content.

According to the soil sensor 1 and the soil measurement method according to the embodiment, the following operational effects can be obtained.

The soil 100 can be modeled as an electric circuit including the resistance component R and the capacitance component C. The water content W and the total ion concentration N in the soil 100 can be obtained from the resistance component R and the capacitance component C. The resistance component R and the capacitance component C can be obtained from a voltage change occurring at the electrode 3. By using the first time t1 until reaching the first threshold voltages VH1 and VL1 and the second time t2 until reaching the second threshold voltages VH2 and VL2, it is possible to calculate the resistance component R and the capacitance component C that define a voltage change. In order to cause a voltage change, the soil sensor 1 supplies a DC current from the current supply unit 2 to the electrode 3. The DC current is supplied to the soil 100 as a measurement target through the electrode 3. As a result of supplying the DC current, the electrode 3 receives a change in voltage according to the magnitude of the resistance component R and the capacitance component C in the soil 100. When calculating the resistance component R and the capacitance component C, a DC current is supplied to the measurement target. As a result, even when changes in the resistance component R and the capacitance component C are large, it is possible to obtain a good voltage change by adjusting the magnitude of the DC current. Therefore, the soil sensor 1 can measure the characteristic values of the soil 100 over a wide measurement range.

In the soil sensor 1 and the soil measurement method, a DC current is applied to the soil 100, and a voltage change obtained as a result of the application is obtained. In the soil sensor 1 and the soil measurement method, the resistance component R and the capacitance component C are calculated using the voltage change. The soil sensor 1 and the soil measurement method can actively change the conditions of the DC current applied to the soil 100 to conditions in which the resistance component R and the capacitance component C can be easily detected. Therefore, it is possible to detect a wide range of the resistance component R and the capacitance component C.

The soil sensor 1 can obtain a wide range of water content change and ion concentration change. In the application of a sine wave of a single frequency, it may not be possible to measure soil or water in which the capacitance component C and the resistance component R change greatly. Therefore, the soil sensor 1 and the soil measurement method can extend the range in which measurement can be performed by actively switching to the conditions in which the capacitance component C and the resistance component R can be detected.

The information conversion unit 11 outputs a pulse signal (frequency information) indicating that the absolute value of the measured voltage VM has reached the absolute value of the first threshold voltage or the second threshold voltage. The current supply unit 2 switches the direction of the DC current according to the pulse signal. According to this configuration, time information regarding the temporal change of the voltage is converted into frequency information. By converting the time information regarding the temporal change of the voltage into the frequency information, it is possible to improve the noise resistance.

In other words, the soil sensor 1 and the soil measurement method convert a voltage change into the number of square wave pulses (frequency) of a digital signal. As a result, in the field measurement of a noisy soil environment, stable signal transmission is performed. As a result, a wide range of water content and ion concentration can be detected by the soil sensor 1 and the soil measurement method. In addition, the soil sensor 1 and the soil measurement method can perform stable signal transmission by digital signal conversion.

In short, the digit of the resistance component R may change widely from 100Ω to 10 MΩ. Here, the soil sensor 1 and the soil measurement method convert the voltage into the number of square wave pulses. That is, the voltage information is converted into frequency information. As a result, a change in the digit of the resistance component R can be handled as a change in the digit of the frequency. Therefore, conversion into a wide range of digital signals can be performed by one detector. In other words, in the soil sensor 1 and the soil measurement method, it is not necessary to prepare a plurality of measurement ranges when obtaining a voltage.

Incidentally, the known soil sensor has a limit of a measurement frequency. In the measurement of the soil water content and the ion concentration, when measuring the impedance of water, a sine wave of a high frequency of 100 kHz or more may be applied to water. However, it is difficult for the known soil sensor to generate a high frequency sine wave of 100 kHz or more. Therefore, the measurement itself is difficult.

On the other hand, the current supply unit 2 of the soil sensor 1 includes the first constant current source 7 that outputs a positive DC current, a second constant current source 8 that outputs a negative DC current, and the switch 9 for selectively connecting one of the first constant current source 7 and the second constant current source 8 to the electrode 3 according to a pulse signal. According to this configuration, it is possible to supply a pulsed current that changes periodically to the soil 100. The pulsed current has no limitation in a high frequency range such as a sine wave. As a result, a current having a high frequency can be supplied to the soil 100. Therefore, it is possible to reduce the influence of an additional capacitance component (so-called electric double layer) that may exist before and after the soil 100. As a result, the soil sensor 1 can obtain a better voltage change.

The information conversion unit 11 includes the first comparator 16, which is connected to the electrode 3 to compare the positive first threshold voltage with the measured voltage VM, and the second comparator, which is connected to the electrode 3 to compare the negative first threshold voltage with the measured voltage VM. According to this configuration, the first time t1 and the second time t2 can be converted into frequencies with a simple configuration.

The information conversion unit 11 has the logic circuit unit 14 connected to the first comparator 16 and the second comparator 17. According to this configuration, time information can be converted into frequency information with a simpler configuration.

The logic circuit unit 14 is a flip-flop circuit. According to this configuration, time information can be converted into frequency information with a simpler configuration.

The information conversion unit 11 has the buffer 12e provided between the output of the first comparator 16 and the impedance calculation unit 18. According to this configuration, it is possible to reduce the influence of noise on the information transmitted from the information conversion unit 11 to the impedance calculation unit 18.

Although the embodiment of the present invention has been described, the present invention is not limited to the above embodiment.

For example, as illustrated in FIG. 1, the soil sensor 1 may include a monitoring terminal 41 connected to the electrode 3.

As illustrated in FIG. 1, the soil sensor 1 may include a capacitance component 42 connected to the reference potential 101 between the electrode 3 and the processing unit 4.

The processing unit 4 may include an amplifier. The amplifier amplifies the measured voltage VM supplied to the first comparator 16 and/or the second comparator 17. The position where the amplifier is provided is not limited as long as the position is between the electrode 3 and the first comparator 16 and/or between the electrode 3 and the second comparator 17. For example, the amplifier may be provided between the input 4a of the processing unit 4 and the input 11a of the information conversion unit 11. According to the amplifier, it is possible to eliminate a reading error from the threshold voltage of the comparator when the measured voltage VM is small.

For example, the soil sensor 1 and the soil measurement method may be used for agriculture. In agriculture, the soil water content and the ion concentration are important information. The soil water content has a large effect on crop growth. The ion concentration affects the nutrient concentration in soil. Therefore, precision agriculture requires the collection of information regarding crops and their environment and the use of the collected information for agricultural production management. Therefore, it is necessary to measure soil information. According to the soil sensor 1 and the soil measurement method, it is possible to provide accurate soil information in a wide measurement range. As a result, the present invention can be appropriately used for precision agriculture.

Since the soil sensor 1 and the soil measurement method have a wide measurement range, the soil sensor 1 and the soil measurement method may be used for prediction of a landslide disaster. For example, the soil sensor 1 and the soil measurement method may be used for evaluating the degree to which a landslide disaster can occur. For example, by obtaining the water content contained in the soil on the slope using the soil sensor 1 and the soil measurement method, it is possible to evaluate the degree to which a landslide disaster can occur. In order to obtain the water content, the soil sensor 1 and the soil measurement method can be appropriately used.

Figure 10:
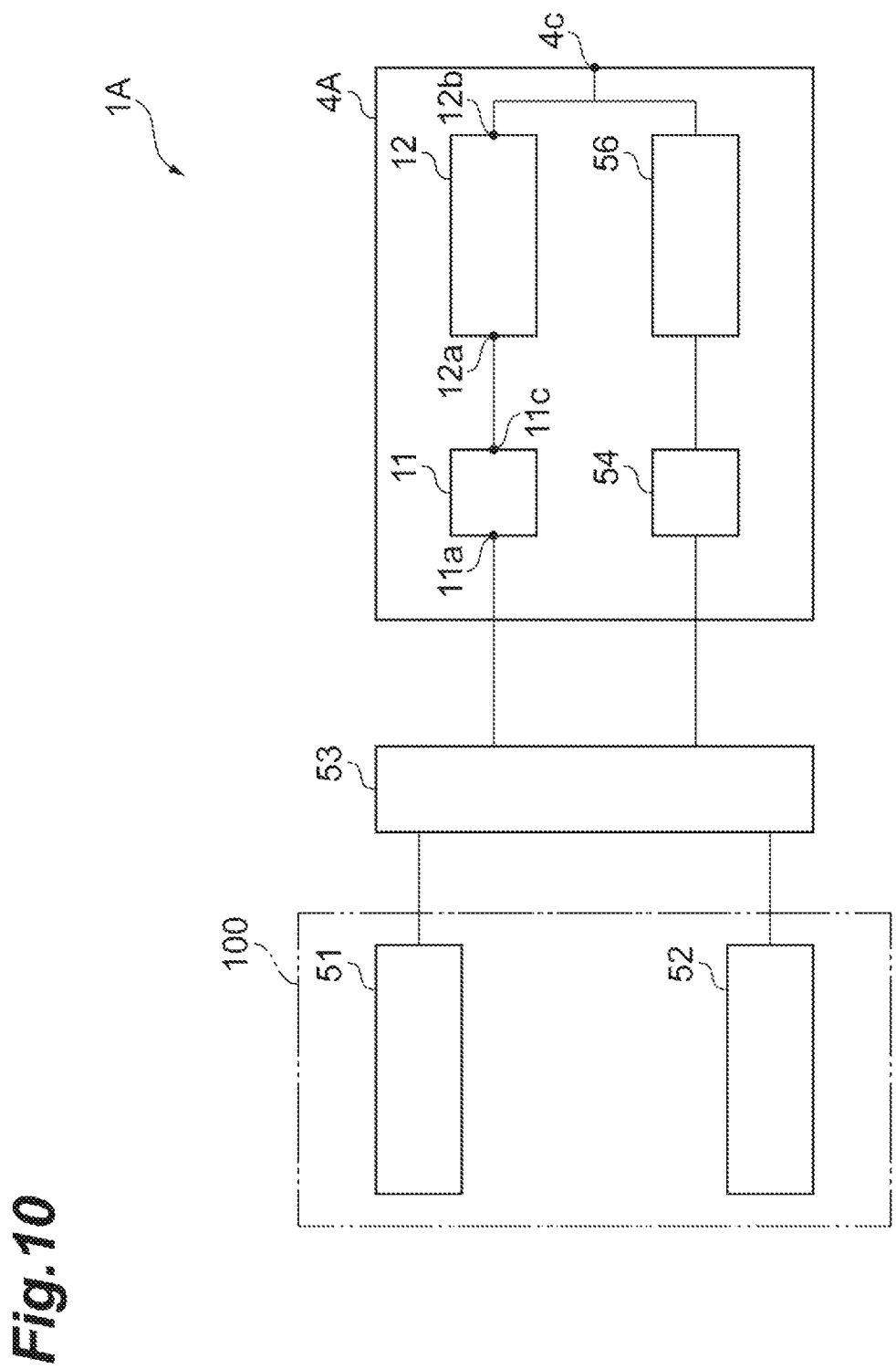
FIG. 10 is a diagram illustrating a configuration of a soil sensor according to a modification example.

For example, as illustrated in FIG. 10, a soil sensor 1A may include a plurality of sensors for obtaining different characteristic values. The soil sensor 1A has a sensor 51 (first sensor unit) for obtaining the water content and the total ion concentration, and a sensor 52 (second sensor unit, temperature measurement unit) for obtaining the temperature. The sensor 51 is configured by the above-described current supply unit 2, electrode 3, and the like, and outputs a voltage (first measured voltage) according to the water content and the total ion concentration. The sensor 52 is embedded in the soil 100, and outputs a voltage (second measured voltage) according to the temperature of the soil 100. For example, the sensor 52 may be a temperature sensor using a diode or a temperature sensor using an n-mos. In addition, the soil sensor 1A has a switch circuit 53 connected to the sensors 51 and 52. The switch circuit 53 selectively connects the sensors 51 and 52 to a processing unit 4A. For example, when obtaining the water content and the total ion concentration by the soil sensor 1A, the sensor 51 is connected to the processing unit 4A. In addition, when obtaining the temperature by the soil sensor 1A, the sensor 52 is connected to the processing unit 4A. The processing unit 4A includes an information conversion unit 54 (temperature information conversion unit) and a calculation unit 56 (temperature calculation unit) that are added in addition to the information conversion unit 11 and the calculation unit 12 for converting the first measured voltage into the first frequency information. The calculation units 12 and 56 configure a measurement value calculation unit. The information conversion unit 54 converts the voltage received from the switch circuit 53 into second frequency information (temperature frequency information). Then, the information conversion unit 54 provides the second frequency information to the calculation unit 56. In addition, the processing unit 4A includes one information conversion unit 11, and the information conversion unit 11 may be shared. The information conversion unit 54 is a so-called VF conversion circuit, and has approximately the same configuration as the information conversion unit 11. The calculation unit 56 converts the frequency information provided from the information conversion unit 54 into temperature information. The calculation unit 56 records conversion information such as a function or a data sheet that defines the correspondence between frequency and temperature. The calculation unit 56 converts frequency information into temperature information using these pieces of information.

Experimental Example 1

In Experimental Example 1, a circuit simulation was performed. In this simulation, a model simulating the circuit illustrated in FIG. 1 was used. The capacitance component C of the soil 100 was set to 500 pF. The resistance component R was set to 1 MO. The magnitude of the DC current was set to 6 µA. The first threshold voltage VH1 was set to +1 V. The first threshold voltage VL1 was set to −1 V. FIG. 8(*a*) shows the result of the simulation. In FIG. 8(*a*), a graph G8*a* shows the measured voltage VM received by the input 11*a* of the information conversion unit 11. A graph G8*b* shows a pulse signal received by the output 11*c* of the information conversion unit 11. Referring to the graph G8*a*, it was found that the measured voltage VM was folded around +1 V and −1 V. Referring to the graph G8*b*, it was found that the signal level of the pulse signal changed in synchronization with the timing at which the measured voltage VM was folded. As a result, it was found that the circuit illustrated in FIG. 1 can perform a correct operation. According to the above conditions, the frequency of the pulse signal was 2.91 kHz.

Experimental Example 2

The circuit illustrated in FIG. 1 was created using discrete components. Then, the characteristics of the created circuit were checked. FIG. 8(*b*) shows the characteristics of the circuit. In FIG. 8(*b*), a graph G8*c* shows the measured voltage VM received by the input 11*a* of the information conversion unit 11. A graph G8*d* shows a pulse signal provided by the output 11*c* of the information conversion unit 11. Referring to the graph G8*c* and the graph G8*d*, it was found that the same tendency as in the simulation result (FIG. 8(*a*)) appeared. As a result, it was found that an actual circuit created based on the circuit illustrated in FIG. 1 can perform a correct operation. In addition, according to Experimental Example 2, the frequency of the pulse signal was 2.95 kHz.

Experimental Examples 3 and 4

When the circuit used in Experimental Example 2 was immersed in water, it was confirmed that the circuit operated properly. As a component corresponding to the electrode 3, a metal plate immersed in water was used instead of a discrete component. The water as a measurement target was ultrapure water (Experimental Example 3) and water of 100 mS/m (Experimental Example 4). FIG. 8(*c*) shows the result of Experimental Example 3. A graph G8*e* shows the measured voltage VM received by the input 11*a* of the information conversion unit 11. A graph G8*f* shows a pulse signal provided by the output 11*c* of the information conversion unit 11. FIG. 8(*d*) shows the result of Experimental Example 4. A graph G8*g* shows the measured voltage VM received by the input 11*a* of the information conversion unit 11. A graph G8*h* shows a pulse signal provided by the output 11*c* of the information conversion unit 11. Referring to FIGS. 8(*c*) and 8(*d*), it was found that the circuit can generate a pulsed waveform even when the measurement target is water. That is, it was found that the created circuit can perform a correct operation even when the measurement target is water.

Experimental Examples 5 and 6

Using the circuit used in Experimental Example 2, the relationship between the capacitance component C and the resistance component R simulating the soil 100 and the frequency of the pulse signal was checked. In Experimental Example 5, the resistance component R was set to 1 MΩ. The capacitance component C was set to 100 pF, 200 pF, 300 pF, 400 pF, and 500 pF. In Experimental Example 6, the resistance component R was set to 10 kΩ. The capacitance component C was set to 100 pF 200 pF, 300 pF, 400 pF, and 500 pF. FIG. 9(*a*) shows the result of Experimental Example 5. FIG. 9(*b*) shows the result of Experimental Example 6. By checking FIGS. 9(*a*) and 9(*b*), the tendency that the frequency increased as the capacitance component C decreased was confirmed. That is, it was confirmed that the time required to reach the threshold voltage was shortened. By comparing FIGS. 9(*a*) and 9(*b*) with each other, it was confirmed that the frequency decreased as the resistance component R decreased. From these results, it was found that the designed circuit illustrated in FIG. 1 can perform a correct operation.

REFERENCE SIGNS LIST

1: soil sensor, 2: current supply unit, 2*a*: input, 2*b*: output, 3: electrode (electrode unit), 4: processing unit, 4*a*: input, 4*b*, 4*c*: output, 6: current setting unit, 7: first constant current source, 8: second constant current source, 9: switch, 11: information conversion unit, 11*a*: input, 11*b*, 11*c*, 11*d*: output, 12: calculation unit, 12*a*: input, 12*b*: output, 13: comparison unit, 13*a*: input, 13*b*, 13*c*: output, 14: logic circuit unit, 14*a*, 14*b*: input, 14*c*, 14*d*: output, 14*e*: buffer, 15: threshold voltage supply unit, 16: first comparator, 17: second comparator, 18: impedance calculation unit, 19:

water content calculation unit, 21: total ion concentration calculation unit, 22: probe, 23: cable, 24: computer, 26: sensor chip, 41: monitoring terminal, 42: capacitance component, 100: soil, 101: reference potential, C: capacitance component, R: resistance component, W: water content, N: total ion concentration, VM: measured voltage, VH1, VL1: first threshold voltage, VH2, VL2: second threshold voltage, I: DC current, t1, t1H, t1L: first time, t2, t2H, t2L: second time, G6P, G6Q: pulse signal.

The invention claimed is:

1. A soil sensor, comprising:
a current supply unit that outputs a first direct current (DC) current having a positive current value and a second DC current having a negative current value;
an electrode unit that is connected to the current supply unit and is disposed in soil as a measurement target to selectively supply the first DC current and the second DC current to the measurement target; and
a processing unit that is connected to the electrode unit and obtains a water content and a total ion concentration in the measurement target using a temporal change of a measured voltage, which is generated in the electrode unit, while the first DC current or the second DC current is being supplied to the measurement target,
wherein the processing unit includes:
an information conversion unit that converts time information from when the current supply unit starts supplying the first DC current or the second DC current to the target when an absolute value of the measured voltage reaches an absolute value of a threshold voltage into frequency information, which is a pulse signal, by means of a logic circuit unit, by determining whether or not the absolute value of the measured voltage has reached the absolute value of the threshold voltage using the temporal change of the measured voltage, by means of a comparison unit;
an impedance calculation unit that obtains an impedance of the measurement target using the frequency information, the threshold voltage, and the first DC current or the second DC current;
a water content calculation unit that obtains the water content using the impedance; and
a total ion concentration calculation unit that obtains the total ion concentration using the impedance, wherein the current supply unit includes a first constant current source that outputs the first DC current, a second constant current source that outputs the second DC current, and a switch that selectively connects one of the first constant current source and the second constant current source to the electrode unit, and
the switch receiving the pulse signal selectively connects one of the first constant current source and the second constant current source to the electrode unit.

2. The soil sensor according to claim 1,
wherein the information conversion unit outputs the pulse signal indicating that the absolute value of the measured voltage has reached the absolute value of the threshold voltage, and
the current supply unit switches a direction of the DC current according to the pulse signal.

3. The soil sensor according to claim 1,
wherein the comparison unit provided in the information conversion unit includes:
a first comparator that is connected to the electrode unit and compares the threshold voltage that is positive with the measured voltage; and
a second comparator that is connected to the electrode unit and compares the threshold voltage that is negative with the measured voltage.

4. The soil sensor according to claim 3,
wherein the information conversion unit includes the logic circuit unit connected to the first comparator and the second comparator.

5. The soil sensor according to claim 4,
wherein the logic circuit unit includes a flip-flop circuit.

6. The soil sensor according to claim 3,
wherein the processing unit further includes an amplifier that is disposed between the electrode unit and the first comparator to amplify the measured voltage.

7. The soil sensor according to claim 3,
wherein the information conversion unit includes a buffer provided between an output of the first comparator and the impedance calculation unit.

8. The soil sensor according to claim 1, further comprising:
a temperature measurement unit that is disposed in the measurement target and that outputs a voltage corresponding to a temperature of the measurement target and supplies the voltage to the processing unit,
wherein the processing unit includes:
a temperature information conversion unit that receives the voltage supplied from the temperature measurement unit and converts the received voltage into temperature frequency information; and
a temperature calculation unit that calculates a temperature of the measurement target using the temperature frequency information output from the temperature information conversion unit.

9. The soil sensor according to claim 8,
wherein the temperature measurement unit includes a diode, and
the current supply unit supplies a current to the diode.

10. A soil measurement method, comprising:
a step of arranging an electrode unit, which is connected to a current supply unit that outputs a direct current (DC) current, in soil as a measurement target and then supplying the DC current to the measurement target through the electrode unit; and
a step of obtaining a water content and a total ion concentration in the measurement target using a temporal change of a measured voltage, which is generated in the electrode unit, while the DC current is being supplied to the measurement target,
wherein the step of obtaining the water content and the total ion concentration includes:
a step of converting time information from when the current supply unit starts supplying the DC current to when an absolute value of the measured voltage reaches an absolute value of a threshold voltage into frequency information by determining whether or not the absolute value of the measured voltage has reached the absolute value of the threshold voltage using the temporal change of the measured voltage;
a step of obtaining an impedance of the measurement target using the frequency information, the threshold voltage, and the DC current;
a step of obtaining the water content using the impedance; and
a step of obtaining the total ion concentration using the impedance, wherein the step of supplying the DC current to the measurement target includes reversing a polarity of the DC current supplied to the measurement target when the measured voltage reaches the threshold voltage.

11. A soil sensor, comprising:

a first sensor unit that is disposed in soil as a measurement target and outputs a first measured voltage corresponding to a water content and a total ion concentration in the soil;

a second sensor unit that is disposed in soil as the measurement target and outputs a second measured voltage corresponding to a temperature of the soil;

an information conversion unit that is selectively connected to the first sensor unit and the second sensor unit and that converts the first measured voltage into first frequency information and converts the second measured voltage into second frequency information; and a measurement value calculation unit that is connected to the information conversion unit and that obtains the water content and the total ion concentration using the first frequency information and obtains the temperature using the second frequency information.

* * * * *